(12) United States Patent
Guilbaud

(10) Patent No.: US 8,802,133 B2
(45) Date of Patent: Aug. 12, 2014

(54) SILICONE SCAR TREATMENT PREPARATION

(75) Inventor: Paul Guilbaud, Largo, FL (US)

(73) Assignee: Advanced Bio-Technologies, Inc., Suwanee, GA (US)

( * ) Notice: Subject to any disclaimer, the term of this patent is extended or adjusted under 35 U.S.C. 154(b) by 213 days.

(21) Appl. No.: 13/548,899

(22) Filed: Jul. 13, 2012

(65) Prior Publication Data
US 2013/0183256 A1 Jul. 18, 2013

Related U.S. Application Data

(63) Continuation of application No. 12/487,489, filed on Jun. 18, 2009, now abandoned.

(51) Int. Cl.
| | | |
|---|---|---|
| *A61K 8/37* | (2006.01) | |
| *A61K 8/25* | (2006.01) | |
| *A61K 47/34* | (2006.01) | |
| *A61K 47/22* | (2006.01) | |
| *A61K 31/573* | (2006.01) | |
| *A61K 31/618* | (2006.01) | |
| *A61K 8/891* | (2006.01) | |
| *A61K 31/12* | (2006.01) | |
| *A61Q 17/04* | (2006.01) | |
| *A61K 31/216* | (2006.01) | |
| *A61K 47/02* | (2006.01) | |
| *A61K 9/00* | (2006.01) | |

(52) U.S. Cl.
CPC ............... *A61K 47/34* (2013.01); *A61K 31/573* (2013.01); *A61K 31/618* (2013.01); *A61K 8/891* (2013.01); *A61K 9/0014* (2013.01); *A61K 8/37* (2013.01); *A61K 47/22* (2013.01); *A61K 31/12* (2013.01); *A61Q 17/04* (2013.01); *A61K 31/216* (2013.01); *A61K 47/02* (2013.01); *A61K 8/25* (2013.01); *Y10S 514/871* (2013.01); *Y10S 514/928* (2013.01)
USPC ............ 424/445; 424/70.12; 424/59; 424/60; 514/179; 514/772; 514/784; 514/785; 514/871; 514/928

(58) Field of Classification Search
CPC ... A61K 31/12; A61K 31/573; A61K 31/618; A61K 8/25
USPC ........... 424/445, 70.12, 59, 60; 514/179, 772, 514/784, 785, 871, 928
See application file for complete search history.

(56) References Cited

U.S. PATENT DOCUMENTS

| | | | |
|---|---|---|---|
| 5,292,530 | A | 3/1994 | McCrea et al. |
| 5,389,092 | A | 2/1995 | Guillemet et al. |
| 5,556,699 | A | 9/1996 | Niira et al. |
| 5,741,509 | A | 4/1998 | Kushner |
| 5,833,998 | A | 11/1998 | Biedermann et al. |
| 5,972,320 | A | 10/1999 | Moloney et al. |
| 6,155,265 | A | 12/2000 | Hammerslag |
| 6,183,766 | B1 | 2/2001 | Sine et al. |
| 6,827,929 | B1 | 12/2004 | Lord et al. |
| 2004/0175414 | A1 | 9/2004 | Berlat |
| 2006/0110415 | A1 | 5/2006 | Gupta |
| 2008/0292560 | A1 | 11/2008 | Tamarkin et al. |
| 2008/0299220 | A1 | 12/2008 | Tamarkin et al. |
| 2009/0143333 | A1 | 6/2009 | Palefsky et al. |
| 2010/0092409 | A1 | 4/2010 | Amin et al. |
| 2010/0196454 | A1 | 8/2010 | Keller |
| 2011/0009374 | A1 | 1/2011 | Keller |

FOREIGN PATENT DOCUMENTS

| | | |
|---|---|---|
| JP | 04-009327 | 1/1992 |
| JP | 09-194350 | 7/1997 |
| WO | WO-97/03710 | 2/1997 |
| WO | WO-00/47183 | 8/2000 |
| WO | WO-2004006972 | 1/2004 |
| WO | WO 2005/065136 A3 | 7/2005 |
| WO | WO 2007/133720 A2 | 11/2007 |

OTHER PUBLICATIONS

Merck Index (9th Ed.) Entry No. 9812: Zinc Oxide, 1976.
Dow Corning MSDS for silicone blend 225 (i.e. DC-225), Mar. 26, 2007.
Thixin R/Thicin R—properties bulletin: Elementis Specialities, Inc. 2009.

*Primary Examiner* — Mina Haghighatian
(74) *Attorney, Agent, or Firm* — Shumaker, Loop & Kendrick, LLP

(57) ABSTRACT

Disclosed is 1) a method for greatly increasing the solubility of useful actives in siloxane matrix-forming preparations, and 2) the associated preparations, themselves. Volatilizing coagents are utilized to give novel gels containing heretofore siloxane-insoluble additives.

13 Claims, 1 Drawing Sheet

SILICONE SCAR TREATMENT PREPARATION

CROSS-REFERENCE TO RELATED APPLICATIONS

This application is a continuation of application Ser. No. 12/487,489, filed Jun. 18, 2009.

BACKGROUND

Lacerations and other wounds which compromise the integrity of the skin are common enough that most people have experienced them, from the mundane, such as a skinned knee, to the life-threatening, such as a stab wound or a serious burn. Many breaks to the skin raise the possibility of disfigurement through scarring.

The development of scar tissue is a defensive response to an injury in that it repairs a breach in the skin, eliminating a site of potential infection and reinjury. However, the rampant formation of scar tissue can result in a tough dermal surface lacking the color or consistency of the surrounding skin. Because the flexibility and elasticity of scar tissue differs from that of natural skin, scar tissue can ultimately limit the lives of those who are affected. Scar tissue is generally tougher than the skin tissue in the surrounding area. This is especially true of scar tissue where the skin is subjected to deformation and elastic stresses, such as on or behind the knee or elbow. Such areas can be subject to tear at the skin/scar tissue border. Scar tissue, particularly new scars, covering areas having natural grooves to facilitate bending, such as the lines on the palms of the hands, are often weak at these flex lines. Stretching caused by opening and closing the hand can rupture the scar tissue at these natural grooves, resulting in an accumulation of scar tissue on either side of the groove, causing newly formed tissue in the groove even to have even greater susceptibility to tearing with hand motion. In general, the natural topography of a wound site can increase the likelihood of retearing, resulting in long healing times.

The lack of flexibility and suppleness of scar tissue is complicated by the fact that scarred areas can become naturally contracted during and after formation as the scar becomes thick, leathery, and inelastic. As a result, the motion of those who have extensive skin injury, such as burn victims, can be severely restricted. A severely burned hand can become frozen in a grasp. Scar tissue due to burns around the waist can prevent torsional motions that most people take for granted.

Some preparations for treating wounds are formulated to have a positive effect on the properties of the scar tissue formed during healing. For example, some wound dressings have functions such as reducing wound drying and preventing ultraviolet light exposure. Such formulations can prevent repeated cracking and drying, resulting in, among other things, the formation of scar tissue having improved flexibility, elasticity and color characteristics relative to scar tissue formed in the absence of the formulation.

Some formulations are made of strictly organic materials, such as gels. Gels have properties which make them suitable as wound dressings. They can cool wounds by contacting them directly, yet keep them free from contamination. Another useful property of gels is their consistency: many gels are similar to skin in elasticity and deformability, and they can bend, bunch and stretch with the skin and tissue surfaces to which they are attached without causing tearing or stress at the site of the healing wound.

However, gels can dry out rapidly with time, break down structurally and/or chemically, and they generally must be reapplied, which can be a painful process for the patient, especially if the consistency of the dressing has become stiff due to drying. Some gels can absorb moisture, developing a soft or liquid consistency. Once the gel consistency has been compromised, the potential for bacterial infection increases.

Siloxane gels have been found to be generally superior to other types of gel products in the treatment of wounds and scar tissue. Siloxane gels function by forming a silicone-based polymer matrix over a wound site. Polymer precursors, such as dimethicone, dimethicone crosspolymer, and other siloxanes, are contained in a spreadable preparation which is applied to a wound site. Some polymer precursor formulations include fumed silica. The preparation also contains a volatile component which begins to evaporate upon the application of the preparation to a wound site. The polymer matrix begins to form upon the evaporation of volatile compounds from the spreadable preparation. The preparations are, in many cases, thixotropic, particularly if the formulation contains fumed silica. Thixotropic formulations change from a stiff consistency to a fluid-like consistency upon the application of stress, such as application to a wound, and revert to a stiffer, less fluid consistency once the stress is removed. This property gives siloxane gel precursor formulations the ability to spread easily into a relatively thin layer over a wound and remain in place without oozing away from the wound site, all with a minimum of stress and shear at the wound site.

Another advantage of siloxane gels is that some have been shown to have a beneficial effect on the properties of scar tissue as it is being formed, diminishing the degree of scarring and improving the texture of scar tissue that does form, such that the ultimate appearance of the healed wound is more like surrounding skin. For instance, some siloxane preparations, when applied to developing or newly formed scar tissue, have demonstrated the ability to cause excellent fading, and even near disappearance of the scar with constant application.

Unlike other spreadable preparations on the market for aiding in the healing of wounds, once a degree of polymerization has taken place to form the siloxane polymer matrix, the resultant gel generally has the ability to retain its consistency over time. Furthermore, the unapplied product can be easier to store and use than other types of gels because it can be applied as siloxane polymer matrix precursors which do not "set" until after application.

Because siloxane gels have such beneficial effects upon developing scar tissue, it is desirable that such a preparation also have the ability to include additives which impart additional useful functions to the gel. For example, while the foregoing silicone-based formulations demonstrate superior scar reduction properties, developing scar tissue is susceptible to change in color and/or texture, as well as other types of damage, such as thermal damage, upon exposure to ultraviolet and other wavelengths of radiation. It is thus desirable to incorporate sun screening compounds into the formulation which will be retained upon matrix formation. Furthermore, burns and other injuries which are best served by the topical application of gels can continue to be very painful, even after the wound has begun to scar over. However, the application of the matrix forming preparation can prevent the topical application of pain relievers: unlike bandage-type coverings, most topical gels cannot be simply lifted and resituated. It can thus desirable that matrix forming preparations comprise at least one pain alleviating compound.

Unfortunately, the use of siloxane matrix precursors has severely limited the variety of additives which can be included in silicone wound dressings. Many desirable additives are not readily solvated in the mix of matrix precursors, such as dimethicone and other siloxanes which comprise the spreadable preparation. For example, many effective and commonly used sunscreen additives, such as, for example, Octocrylene, Octinoxate, Octisalate and Oxybenzone may not sufficiently dissolve in the pre-polymerized preparation. Other examples of desirable additives having poor solubility in the pre-polymerization preparation include cortisone-type compounds which reduce pain and inflammation, such as, for example, Hydrocortisone acetate.

A method exploiting the advantages of siloxane matrix-forming wound preparations, yet allowing the inclusion of otherwise insoluble additives in silicone wound dressing formulations would be welcomed as a significant advance in the art of wound dressing preparation.

BRIEF DESCRIPTION OF THE INVENTION

It has been found, surprisingly, that the use of certain volatile coagents (in addition to the volatile component) with certain actives, which are otherwise of limited or no solubility in the matrix precursors, enables the incorporation of the actives into a silicone matrix. This is all the more surprising in that the complex which enables the incorporation of the active into the forming matrix actually retains a good degree of volatility, even though complexed with the active, and even though it would be expected that the developing matrix would hinder the ability of the complexed coagent to evaporate. Surprisingly, the volatile coagent is not incorporated within the matrix with the active. Instead, the insoluble active, which is insoluble in the matrix precursors without the coagent, remains incorporated within the matrix during its formation, even though the volatile coagent does not remain complexed to the active, but disjoins and is lost to evaporation. Even more surprising, the active can have mobility within the matrix resulting in the ability to migrate through the gel to the wound site, as evidenced by the effectiveness of analgesic additives. Furthermore, it would be expected that the vapor pressure of the volatile coagent would be reduced upon complexing with the active, and by being incorporated, with the active, within the developing siloxane matrix. Yet it retains sufficient vapor pressure such that it can evaporate away cleanly. The use of volatile coagents, such as those identified herein, permits the incorporation of diverse additive types into silicone matrix-forming formulations. The present invention enables the incorporation of insoluble actives into a mixture of silicon precursors, greatly extending the usefulness of siloxane gel wound healing technology.

DETAILED DESCRIPTION OF THE INVENTION

Siloxane Matrix Precursors

Figure 1:
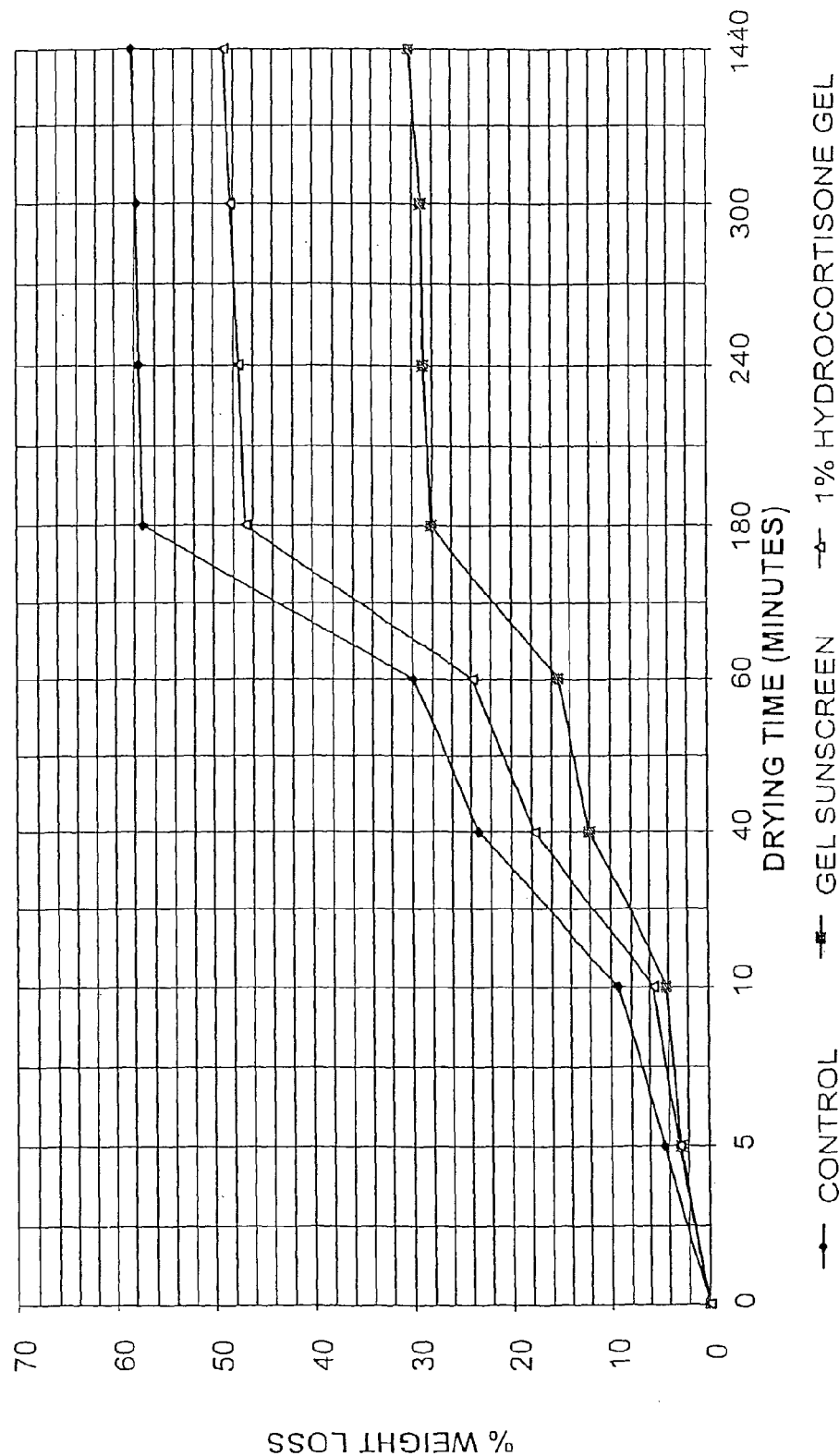
FIG. 1—Drying test results. The lowest, middle and highest curves graphically depict the drying results of the sunscreen, analgesic and control gels respectively.

The matrix forming composition of the present invention comprises siloxane matrix precursors, a volatile component, an active component, and a volatile coagent. The volatile component and volatile coagent partially or fully evaporate from the composition once the composition is applied to a wound or scar site, leaving behind 1) components which participate in matrix formation as well as 2) one or more active components which reside in the matrix. Generally, the components which participate in the matrix formation are one or more siloxanes, one or more of which have organic characteristics, i.e., comprising organic components, such as bearing hydrocarbyl groups. Preferred are polydimethylsiloxanes such as dimethicone and dimethicone cross polymer. A polymer matrix can be formed with the use of other polydimethyl siloxanes instead of or in addition to dimethicone and dimethicone crosspolymer. In particular, it is believed that polymerization involving other polysiloxanes, and in particular, other dialkylpolysiloxanes, can form a matrix exhibiting the advantages of the present invention when used with the volatile components, volatile coagents and actives listed below. Such matrices are within the ambit of the present invention. The fumed silica gives the prepolymerized composition a thixotropic consistency. Fumed silica also participates structurally in the gel, but its contribution to or participation in the polymerization process, if any, is unclear. Provided that a volatile component is present, the matrix precursors in the preparation generally can be stored at room temperature (25 K) for extended periods of time, such as 1, 2, 4, 6, 12 months or even longer without undergoing significant polymerization. It is preferred that the matrix precursors comprise a crosspolymer component, such as dimethicone crosspolymer, as well as dimethicone. In some embodiments, the siloxane component is present in weight percentages in the range of from about 25 to 60 wt %. In preferred embodiments, the siloxane component is present in the range of from 30 to 50 wt %. In more preferred embodiments, the siloxane component is present in amounts in the range of from about 35 to 45 wt %. The preferred siloxane component is dimethicone. The cross polymer component is preferably present in amounts in the range of from about 0.5 to about 8 wt %, and more preferably in the range of from about 1.5 to 5 wt %.

Volatile Component

The composition of the present invention comprises a volatile component (distinguished from volatile coagent, discussed below). The volatile component generally begins to vaporize upon application of the composition to the wound site. In some embodiments, the formation of the siloxane matrix can begin immediately upon commencement of evaporation, proceeding with further evaporation. In other embodiments, the siloxane matrix begins to form appreciably at some time during the evaporation of the volatile component, with only negligible formation prior to the time. In preferred embodiments, the volatile component has limited or no participation in polymerization, but readily solvates or dissolves in the matrix precursors. Preferred examples are volatile siloxane compounds which have little or no participation as reactants in siloxane polymerization. For example, cyclic siloxanes generally exhibit good solvation and volatility characteristics in siloxanes, and their participation in matrix formation is generally relatively low due to the fact that all silane oxygen atoms are unavailable for polymerization. More preferred is a cyclopentasiloxane which bears constituents comprising hydrogen or hydrocarbyl groups of less than four carbon atoms. Constituents comprising hydrogen or hydrocarbyl groups of one carbon atom are most preferred. Preferred amounts of volatile component are in the range of from about 12 to about 45 wt %. More preferred are amounts in the range of from about 15 to 28 wt %, most preferred are amounts in the range of from about 20 to 25 wt %.

The volatile component is preferably present in amounts such that the volatile component is more than 50 percent evaporated after 15 minutes at one or more temperatures in the range of from about 30 to 40 C.

In general, the volatile component functions such that upon its partial or entire evaporation, the polymer matrix begins to form. Thus, in some embodiments, the presence of the volatile can act to fully or partially inhibit the polymerization process, such that upon beginning to volatilize, the rate of polymerization increases. In general, the composition of the present invention is not limited to the compounds specifically described above, but broadly comprises compounds which can be used in relative amounts such that they fully or partially inhibit the formation of the siloxane matrix prior to wound application, but begin to evaporate upon the application of the preparation to a wound, having fully or partially evaporated by the completion of siloxane matrix formation. In some embodiments, the volatile component evaporation plateaus with time prior to complete evaporation. In other embodiments, the evaporation of the volatile component continues after the siloxane matrix is completely formed. It is preferable that the volatile component evaporate to within less than 5% of its original weight (storage concentration) within 3 hours, but in some embodiments, the volatile evaporates to within greater than 10, 20 and 30% of its original weight within 3 hours. In some embodiments, the weight percent of the volatile component concentration prior to use and during storage is in the range of from about 5 to about 40%. In other embodiments, the weight percent of the volatile component concentration prior to use and during storage is in the range of from about 15 to about 35%. In preferred embodiments, the volatile component concentration prior to use and during storage is in the range of from about 18 to about 30%.

Actives and Volatile Coagent

The wound healing preparation of the present invention comprises a volatile coagent. Without desiring to be bound by theory, it is thought that the volatile coagent aids in solvating the active in the matrix precursors. It has been found that certain compounds which function as volatile coagents with certain actives have the ability to volatilize appreciably despite the facts that they are chemically associated with the active which is surrounded by a growing matrix, and which itself is not ultimately volatilized.

Many common ultraviolet absorbers are not readily soluble in solutions comprising siloxane matrix precursors. However, it has been found that many ultraviolet absorbers can be solvated in siloxane matrix precursor solutions in the presence of myristate esters. For example, well known Escalol ultraviolet absorbers, having the following diverse structures can be introduced into siloxane matrices:

octocrylene (ISP Escalol 597):

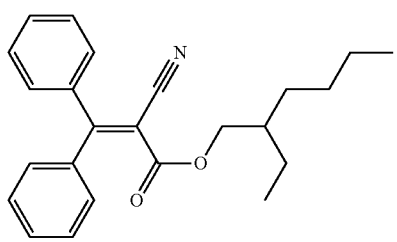 [SMILES: CCCCC(CC)COC(=O)C(C#N)=C(c1ccccc1)c1ccccc1]

octinoxate (ISP Escalol 557):

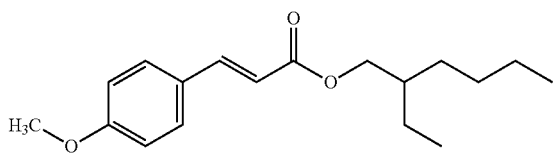 [SMILES: CCCCC(CC)COC(=O)/C=C/c1ccc(OC)cc1]

octisalate (ISP Escalol 587):

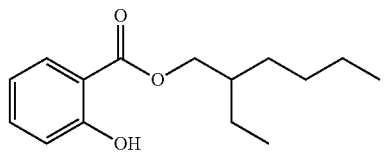 [SMILES: CCCCC(CC)COC(=O)c1ccccc1O]

oxybenzone (ISP Escalol 567):

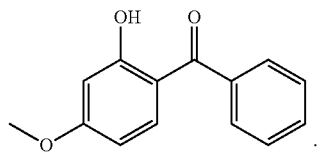 [SMILES: COc1ccc(C(=O)c2ccccc2)c(O)c1]

In one embodiment, the active is an ultraviolet absorbing compound comprising at least one aromatic ring. In a more preferred embodiment the active comprises one or more Escalol compounds, available from ISP Chemicals, and the volatile coagent is an ester of 1) a linear acid having a carbon chain length in the range of from about 6 to 13 carbon atoms and 2) methanol, ethanol, or a secondary alcohol having a total carbon content in the range of from about 3 to about 8 carbon atoms, and the active is an Escalol compound. In a yet more preferred embodiment, the volatile coagent is isopropyl myristate, and the active is octocrylene (ISP Escalol 597), octinoxate (ISP Escalol 557), octisalate (ISP Escalol 587), or oxybenzone (ISP Escalol 567). The sunscreen active or actives present in the formulation can be present in a combined amount in the range of from about 5 to 40 wt %, with amounts in the range of from 15 to 35 wt % being more preferable. In some embodiments, the sunscreen actives are present in amounts in the range of from 25 to 30 wt %.

In general, the volatile coagent preferably comprises an ester of 1) a linear acid having a carbon chain length in the range of from about 6 to 13 carbon atoms and 2) methanol, ethanol, or a secondary alcohol having a total carbon content in the range of from about 3 to about 8 carbon atoms; and more preferably isopropyl myristate; a glycol comprised of a linear chain of three or more carbons and one or more hydroxyl groups; and wherein all hydroxyl groups are on adjacent carbons including an end carbon; and more preferably pentylene glycol; or a substituted or unsubstituted isosorbide; and preferably Dimethyl isosorbide.

Many common anti-inflammatory compounds are based on the steroid compound structure. It has been found that some steroids having low solubility in solutions of siloxane matrix precursors can be solvated in siloxane matrix precursor solutions in the presence of glycol and/or isosorbide compounds.

In one embodiment, the active is a steroid compound, and the volatile coagent is a glycol comprised of a linear chain of three or more carbons and one or more hydroxyl groups; and wherein all hydroxyl groups are on adjacent carbons including an end carbon. In a more preferred embodiment, the volatile coagent is a glycol comprised of a linear chain of from about 3 to 7 carbons and two hydroxyl groups, one attached to each terminal carbon, and the active is a steroid compound. In a yet more preferred embodiment, the volatile coagent is pentylene glycol, and the active is dihydrocortisone acetate.

In one embodiment, the active is a hydrocortisone compound and actives comprising both a glycol compound and an isosorbide compound are used. In a preferred compound, the active is hydrocortisone acetate.

In one embodiment, the active is a hydrocortisone compound and actives comprising both a glycol compound and an isosorbide compound are used. In a preferred compound, the active is Hydrocortisone acetate.

The steroid compound is preferably present in an amount which is in the range of from 0.1 to 8 wt %. More preferred is an amount in the range of from about 0.5 to 3 wt %.

The glycol and the isosorbide are present in amounts in the range of from 5 to 40 wt % percent (combined weight, if both are present). In preferred embodiments, both are present, each in amounts in the range of from 5 to 50 wt %. In other embodiments, the glycol and the isosorbide are present in amounts in the range of from 0 to 15 wt %, with a total weight % in the range of from 10 to 25.

It should be noted that the glycol and isosorbide components can be used with sunscreen actives instead of isopropyl myristate if a deeper penetration is desired.

The composition of the present invention can be prepared by mixing together the matrix precursors such as, for example, fumed silica, dimethicone and dimethicone cross polymer; and the volatile component, such as, for example, cyclopentasiloxane. The foregoing compounds can be mixed together to form a siloxane base. The active component is generally mixed with the volatile coagent to form a mixture which is added to the siloxane base before introducing it into the balance of the composition. In one embodiment, the base contains only cyclopentasiloxane and dimethicone crosspolymer. The mixture is then combined with the base. In general, it is desirable to premix the active with the volatile coagent. However, in some cases, it can be permissible to combine the volatile coagent with all ingredients except the active, adding the active to the preparation in a final step.

Example 1

30 SPF Sunscreen Scar Gel

Scar Gel with 10.0% octocrylene, 7.5% octinoxate, 5.0% octisalate, 6.0% oxybenzone, 8.0% isopropyl myristate, 36% dimethicone, 3.5% fumed silica, 2% dimethicone crosspolymer and 22% cyclopentasiloxane. All percentages wt/wt. octocrylene, octinoxate, octisalate and oxybenzone provide UVA and UVB resistance. They were premixed with isopropyl myristate. The mixture was added to a combination of cyclopentasiloxane and dimethicone crosspolymer. Fumed silica was added next to the overall mixture using a high-shear mixing process (an eductor). The dimethicone is added last, and the mixture is mixed until homogeneous, resulting in a viscous, opaque gel, with no lumps or visible separation. The formulation has an SPF rating of 30 or higher. A drying test was performed (time take to reach a constant weight) (see FIG. 1), and the formulation dried in essentially the same amount of time as the formulation in the absence of the Octocrylene, Octinoxate, Octisalate, Oxybenzone and isopropyl myristate (control formulation). The addition of the sunscreen additives does not appreciably slow the drying of the formulation.

Example 2

Hydrocortisone Acetate Scar Gel

Scar Gel with 1.0% hydrocortisone acetate, 5.0% propylene glycol, 8.0% dimethyl isosorbide, 12.0% pentylene glycol, 45.0% dimethicone, 3.0% fumed silica, 2.0% dimethicone crosspolymer, and 24.0% cyclopentasiloxane. All percentages are wt/wt. The hydrocortisone acetate was premixed into the pentylene glycol, dimethyl isosorbide and propylene glycol and warmed slightly to obtain good mixing before adding to a main batch. The main batch was prepared using a high-shear mixing apparatus (an eductor). No lumps or visible particles were observed. The resulting batch was uniform and slightly opaque. A drying test was performed (see FIG. 1), and the formulation dried in essentially the same amount of time as the formulation in the absence of the dihydrocortisone acetate, propylene glycol and dimethyl isosorbide (control formulation). The addition of the pain/itch reliever does not appreciably slow the drying of the formulation.

Example 3

Experimental Details of the Drying Tests

"30 SPF Sunscreen Silicone Scar Gel" Details

The "30 SPF Sunscreen Silicone Scar Gel," described in Example 1, above, contains the ingredients of the Control Formula Scar Gel" with the addition of the following FDA approved sunscreen actives: 10.0% octocrylene, 7.5% octinoxate, 5.0% octisalate and 6.0% oxybenzone. Also, 8.0% of isopropyl myristate, an emollient ester, was added as a dispersing agent.

"1% Hydrocortisone Acetate Silicone Scar Gel" Details

The "1% Hydrocortisone Acetate Silicone Scar Gel," described in Example 2, above, contains the ingredients of the Control Formula Scar Gel" with the addition of 1% w/w of hydrocortisone acetate, an FDA approved anti-inflammatory agent. Also, 5.0% of propylene glycol (a humectant and skin conditioning agent) and 10.0% of dimethyl isosorbide, a solvent which is a dimethyl ether of an anhydride of an isomer of sorbitol, used for better skin penetration of the hydrocortisone acetate.

Procedure:

The 30 plastic weigh boats were labeled and accurately weighed on an O'Haus EP114 analytical balance. Samples of the Control Formula Scar Gel" were spread out in a thin film on ten plastic weigh boats and the initial weights recorded (T=0). The samples were placed into the Lunaire Environmental Chamber set at 35° C. then removed and weighed at 5, 10, 40, 60, 180, 240, 300 and 1440 minute intervals. The process was repeated for the "30 SPF Sunscreen Silicone Scar Gel" and the "1% Hydrocortisone Acetate Silicone Scar Gel". The results of the comparative study are listed below in TABLE 1—Control Formula Scar Gel Evaporation Study Results; TABLE 2—30 SPF Sunscreen Silicone Gel Evaporation Study Results and TABLE 3—1% Hydrocortisone acetate Silicone Gel Evaporation Study Results. The data from each table has been tabulated and displayed graphically in FIG. 1.

Equipment Used:

(30) 5.25"×3.50"×1.0" plastic weigh boats (1) Calibrated O'Haus EP114 Explorer Pro analytical balance (1) Lunaire Environmental Chamber Model # GE0932M-4 set at 35° C.

Results

TABLE 1

Control Formula Scar Gel
Evaporation Study Results

|  | Empty Weigh Boat (g) | Weight at T = 0 (g) | Weight at T = 5 (g) | Weight at T = 10 (g) | Weight at T = 40 (g) | Weight at T = 60 (g) | Weight at T = 180 (g) | Weight at T = 240 (g) | Weight at T = 300 (g) | Weight at T = 1440 (g) |
|---|---|---|---|---|---|---|---|---|---|---|
| KCG Sample 1 | 3.1621 | 3.3948 | 3.3888 | 3.3863 | 3.3786 | 3.3723 | 3.2731 | 3.2722 | 3.2722 | 3.2715 |
| KCG Sample 2 | 3.2660 | 3.3410 | 3.3385 | 3.3358 | 3.3286 | 3.3278 | 3.3075 | 3.3052 | 3.3031 | 3.3015 |
| KCG Sample 3 | 3.5625 | 3.6590 | 3.6570 | 3.6555 | 3.6472 | 3.6430 | 3.6074 | 3.6067 | 3.6067 | 3.6067 |
| KCG Sample 4 | 3.4816 | 3.5715 | 3.5669 | 3.5621 | 3.5523 | 3.5500 | 3.5213 | 3.5200 | 3.5198 | 3.5201 |
| KCG Sample 5 | 3.5648 | 3.6670 | 3.6596 | 3.6549 | 3.6450 | 3.6412 | 3.6140 | 3.6140 | 3.6132 | 3.6121 |
| KCG Sample 6 | 3.5218 | 3.6102 | 3.6050 | 3.5910 | 3.5660 | 3.5630 | 3.5600 | 3.5599 | 3.5558 | 3.5558 |
| KCG Sample 7 | 3.3741 | 3.4565 | 3.4500 | 3.4459 | 3.4308 | 3.4244 | 3.4101 | 3.4099 | 3.4098 | 3.4098 |
| KCG Sample 8 | 3.4364 | 3.4865 | 3.4849 | 3.4828 | 3.4738 | 3.4688 | 3.4585 | 3.4580 | 3.4583 | 3.4568 |
| KCG Sample 9 | 3.4109 | 3.4724 | 3.4698 | 3.4684 | 3.4585 | 3.4547 | 3.4391 | 3.4383 | 3.4382 | 3.4383 |
| KCG Sample 10 | 3.4674 | 3.5153 | 3.5137 | 3.5113 | 3.5032 | 3.4953 | 3.4903 | 3.4888 | 3.4889 | 3.4888 |

Note:
"T" equals the time interval, in minutes, at which the weights were determined.

TABLE 2

30 SPF Sunscreen Silicone Scar Gel
Evaporation Study Results

|  | Empty Weigh Boat (g) | Weight at T = 0 (g) | Weight at T = 5 (g) | Weight at T = 10 (g) | Weight at T = 40 (g) | Weight at T = 60 (g) | Weight at T = 180 (g) | Weight at T = 240 (g) | Weight at T = 300 (g) | Weight at T = 1440 (g) |
|---|---|---|---|---|---|---|---|---|---|---|
| SSG Sample 1 | 3.3015 | 3.4060 | 3.4032 | 3.4035 | 3.3963 | 3.3931 | 3.3799 | 3.3799 | 3.3793 | 3.3760 |
| SSG Sample 2 | 3.6727 | 3.7753 | 3.7735 | 3.7723 | 3.7651 | 3.7619 | 3.7477 | 3.7477 | 3.7474 | 3.7438 |
| SSG Sample 3 | 2.9276 | 3.0600 | 3.0568 | 3.0574 | 3.0490 | 3.0449 | 3.0259 | 3.0256 | 3.0255 | 3.0215 |
| SSG Sample 4 | 3.2265 | 3.3601 | 3.3571 | 3.3548 | 3.3453 | 3.3410 | 3.3224 | 3.3230 | 3.3230 | 3.3200 |
| SSG Sample 5 | 3.2729 | 3.4094 | 3.4000 | 3.3956 | 3.3829 | 3.3796 | 3.3595 | 3.3598 | 3.3601 | 3.3599 |
| SSG Sample 6 | 3.3635 | 3.5084 | 3.5008 | 3.4980 | 3.4815 | 3.4768 | 3.4557 | 3.4500 | 3.4490 | 3.4700 |
| SSG Sample 7 | 3.5379 | 3.6744 | 3.6721 | 3.6699 | 3.6617 | 3.6579 | 3.6396 | 3.6380 | 3.6373 | 3.6340 |
| SSG Sample 8 | 3.7732 | 3.8523 | 3.8514 | 3.8498 | 3.8426 | 3.8399 | 3.8312 | 3.8307 | 3.8307 | 3.8275 |
| SSG Sample 9 | 3.0460 | 3.1585 | 3.1567 | 3.1549 | 3.1472 | 3.1434 | 3.1301 | 3.1292 | 3.1292 | 3.1260 |
| SSG Sample 10 | 2.9573 | 3.0348 | 3.0333 | 3.0318 | 3.0254 | 3.0221 | 3.0151 | 3.0142 | 3.0140 | 3.0100 |

Note:
"T" equals the time interval, in minutes, at which the weights were determined.

TABLE 3

1% Hydrocortisone Acetate Silicone Scar Gel
Evaporation Study Results

|  | Empty Weigh Boat (g) | Weight at T = 0 (g) | Weight at T = 5 (g) | Weight at T = 10 (g) | Weight at T = 40 (g) | Weight at T = 60 (g) | Weight at T = 180 (g) | Weight at T = 240 (g) | Weight at T = 300 (g) | Weight at T = 1440 (g) |
|---|---|---|---|---|---|---|---|---|---|---|
| HAG Sample 1 | 3.1592 | 3.3599 | 3.3561 | 3.3524 | 3.3365 | 3.3373 | 3.3089 | 3.2583 | 3.2580 | 3.2582 |
| HAG Sample 2 | 3.3183 | 3.4122 | 3.4094 | 3.4063 | 3.3935 | 3.3874 | 3.3742 | 3.3688 | 3.3642 | 3.3639 |
| HAG Sample 3 | 3.4812 | 3.5898 | 3.5860 | 3.5827 | 3.5672 | 3.5611 | 3.5361 | 3.5380 | 3.5380 | 3.5353 |
| HAG Sample 4 | 3.5457 | 3.6612 | 3.6580 | 3.6559 | 3.6394 | 3.6318 | 3.6052 | 3.6058 | 3.6054 | 3.6032 |
| HAG Sample 5 | 3.4292 | 3.5117 | 3.5086 | 3.5071 | 3.4935 | 3.4881 | 3.4719 | 3.4742 | 3.4742 | 3.4751 |
| HAG Sample 6 | 3.6278 | 3.7158 | 3.7118 | 3.7085 | 3.6952 | 3.6885 | 3.6712 | 3.6716 | 3.6723 | 3.6723 |
| HAG Sample 7 | 3.5343 | 3.6615 | 3.6587 | 3.6554 | 3.6400 | 3.6314 | 3.6007 | 3.6030 | 3.6018 | 3.6002 |
| HAG Sample 8 | 3.3502 | 3.4862 | 3.4820 | 3.4778 | 3.4624 | 3.4536 | 3.4204 | 3.4221 | 3.4204 | 3.4201 |
| HAG Sample 9 | 3.5731 | 3.7100 | 3.7070 | 3.7048 | 3.6927 | 3.6831 | 3.6450 | 3.6450 | 3.6450 | 3.6449 |
| HAG Sample 10 | 3.4784 | 3.5971 | 3.5942 | 3.5890 | 3.5806 | 3.5707 | 3.5412 | 3.5430 | 3.5410 | 3.5392 |

Note:
"T" equals the time interval, in minutes, at which the weights were determined.

Calculations

The Percent Weight Loss values were calculated as follows:

$$\% \text{ Weight Loss} = \frac{(\text{Wght. at } T=0 - \text{Wght. of Empty Weigh Boat}) - (\text{Wght. at } T=n - \text{Wght. of Empty Weigh Boat})}{(\text{Wght. at } T=0 - \text{Wght. of Empty Weigh Boat})} \times 100$$

Where n is the weight recorded at times of 5, 10, 40, 60, 180, 240, 300 and 1440 minutes.

Example: The percent weight loss for "1% Hydrocortisone Acetate Silicone Gel at T=5 minutes would be determined accordingly.

$$\% \text{ Weight Loss} = \frac{(3.3599\ g - 3.1592\ g) - (3.3561\ g - 3.1592\ g)}{(3.3599\ g - 3.1592\ g)} \times 100 = 1.8934\%$$

The Percent Weight Loss values were averaged for each of the three products at the appropriate time interval (5, 10, 40, 60, 180, 240, 300 and 1440) and displayed in graphically, see FIG. 1.

CONCLUSION

1. The Control Formula Scar Gel, the "30 SPF Sunscreen Silicone Scar Gel" and the "1% Hydrocortisone Acetate Silicone Scar Gel" all reached relatively stable dried weights at the 180 minute mark.

Example 4

Experimental Details of the SPF Tests

Title: Evaluation of the Static Sun Protection Factor (SPF) of a Sunscreen-Containing Formula
Objective: To measure the Static SPF of an over-the-counter (OTC) sunscreen-containing formula and the 8% Homosalate Standard (HMS) in human volunteers according to the FDA Final Monograph
Test Product: Test Formulation—Expected SPF 30
Study Design: Non-randomized, with blinded evaluations
Results: Five subjects completed the test. The mean SPF of the test product, Test Formulation, was 33.1 (n=5, SD=2.0). The test product would be likely to meet FDA Final Monograph requirements for labeling as Static SPF 30+.[1]
Adverse Experiences: No Adverse Experiences were reported
Summary:
On the first day of the study each subject received a series of UV doses from a xenon arc solar simulator to an unprotected site on the mid-back. On the second day the minimal erythema dose (MED) was determined as the lowest UV dose which produced mild erythema reaching the borders of the exposure site. Then 100 mg of the test product and 100 mg of the HMS standard were applied to separate, adjacent 50 cm2 areas of the mid-back (8% Homosalate (HMS) Standard provided by Cosmetech Laboratories, Inc., Fairfield, N.J.).

The test product had an expected SPF of 30 and the HMS standard sunscreen had an expected SPF of 4. After a 15-minute drying period UV doses ranging from 0.76 to 1.32 times the product of the MED and 30 were administered to the test sunscreen-protected area. UV doses ranging from 0.64 to 1.56 times the product of the MED and 4 were administered to the HMS standard sunscreen-protected area. A series of UV doses were also administered to a second unprotected site. On the third day the MED was determined for the sunscreen-protected sites and the unprotected site. The SPF of each sunscreen was calculated as the ratio of the MED for each sunscreen-protected site to the final MED.

Detailed procedures for determining the Static Sun Protection Factor according to the FDA Sunscreen Monograph) are described in the PROTOCOL.

Details of calibrations for Lamps 1, 2, 7, 8, 10, 13 and 14 are shown in the LAMP CALIBRATIONS.

According to the FDA Final Monograph), the labeled SPF must be calculated as follows:

Labeled SPF=Mean SPF Value–A Rounded down to the nearest whole number

For SPF values>31, the test product may be labeled as SPF 30+
Where
A=ts/sqrt(n) and represents the 95% confidence interval.
t=upper 5% of student's t distribution
s=Standard Deviation
n=Number of Subjects For the panel to be valid, the SPF of the HMS standard sunscreen must fall within the standard deviation range of the expected SPF (i.e. 4.47±1.279) and the 95% confidence interval for the mean SPF of the HMS standard sunscreen must contain the value 4.
Results:

Five subjects, 2 men and 3 women, who provided written, informed consent, completed the study. Subjects who completed all procedures included 2 with skin type I, 2 with skin type II and 1 with skin type III.1 Ages ranged from 21 to 38 years and the mean age was 30.4 (n=5, SD=7.1). Subject demographic and static SPF results are listed in Table 1.

The mean static SPF of the test product, Test Formulation, was 33.1 (n=5, SD-2.0). The mean SPF of the HMS standard was 4.4 (n=5, SD=0.4).
Protocol Deviation:

Protocol Deviations were reported for Subject 04. The Repeat MED and Final SPF evaluations were performed outside of the 22 to 24 hour time frame (21:50 and 21:54 respectively). This Protocol Deviation did not affect study results.
Enrollment:

Subject 03 was disqualified during Day 1 procedures for a prohibited medication and Subjects 05 and 06 were disqualified due to procedural error. Data for these subjects were not included in this report.

TABLE 1

Subject Demographic and Static SPF Data for Test Formulation and HMS Standard
SRL2008-105: Formulated Solutions, LLC HMS

| Subject #* | SRL ID# | Age | Sex | Skin Type | Lamp | Final MED (sec) | Test Formulation SPF | HMS Standard SPF |
|---|---|---|---|---|---|---|---|---|
| 01 | 1792 | 21 | F | I | 8 | 10 | 34.50 | 4.40 |
| 02 | 1702 | 27 | F | II | 2 | 10 | 32.10 | 4.00 |

TABLE 1-continued

Subject Demographic and Static SPF Data for Test Formulation and HMS Standard
SRL2008-105: Formulated Solutions, LLC HMS

| Subject #* | SRL ID# | Age | Sex | Skin Type | Lamp | Final MED (sec) | Test Formulation SPF | HMS Standard SPF |
|---|---|---|---|---|---|---|---|---|
| 04 | 373 | 38 | M | II | 10 | 10 | 30.00 | 4.40 |
| 07 | 1803 | 29 | M | III | 1 | 13 | 34.54 | 4.38 |
| 08 | 895 | 37 | F | I | 2 | 8 | 34.50 | 5.00 |
| | | Mean = 30.4 | | | | | Mean = 33.1 | Mean = 4.4 |
| | | SD = 7.1 | | | | | SD = 2.0 | SD = 0.4 |
| | | n = 5 | | | | | n = 5 | n = 5 |

Subject 03 disqualified—prohibited med
Subject 05 disqualified—procedural error
Subject 06 disqualified—procedural error
Conclusion:
    The test product, Reference Test Formulation, would be likely to meet the FDA Final Monograph requirements for labeling as Static SPF 30+.[1]

REFERENCES

1. U.S. Food and Drug Administration. Sunscreen Drug Products for Over-the-Counter Human Use; Final Monograph; 21CRF Parts 310, 352, 700 and 740. Federal Register 64 (98) May 21, 1999. pp. 27666-27693

Protocol

Objective: To measure the static sun protection factor (SPF) of an over-the-counter (OTC) sunscreen-containing formula according to the FDA Final Monograph[1]
Test Product: Expected SPF 30
Study Design: Non-randomized, with blinded evaluations
Subjects: Five qualified male and/or female volunteers with the skin types I, II and/or III1 will be completed for the test product. With permission from the Sponsor, up to 20 additional subjects may be enrolled to complete requirements for FDA Final Monograph testing.[1]
Introduction:
    The FDA Final Monograph) describes the procedures for determining the Static sun protection factor. The Static SPF is defined by the ratio of the minimal erythema dose of ultraviolet radiation for sunscreen-protected skin to that for unprotected skin. The minimal erythema dose (MED) is the dose of ultraviolet (UV) radiation that produces mild erythema (sunburn) with clearly defined borders, 22 to 24 hours after administration. Timed UV radiation doses were administered using a xenon arc lamp that simulated solar radiation. The technician monitored the output of the solar simulator using a calibrated radiometer to insure that the erythemally effective irradiance was constant. Readings of erythemally effective irradiance were recorded.
Objective:
    The objective of this test was to measure the Static SPF of an over-the-counter (OTC) sunscreen-containing formula according to the FDA Final Monograph[1].
Design:
    This was a non-randomized study with blinded evaluations.
Subjects:
    Subjects included up to 25 healthy male and female volunteers completed per product with skin types I, II and/or III[1] (See below).

| Skin Type | Erythema and Tanning Reactions to First Sun Exposure in Spring* |
|---|---|
| I | Always burns easily; never tans |
| II | Always burns easily; tans minimally |
| III | Burns moderately; tans gradually |
| IV | Burns minimally; always tans well |

*Subject-reported responses to 1 hour of summer sun exposure

Subjects reported any OTC or prescription medication used within the week before and during study participation. Subjects also satisfied the following criteria:
Inclusion Criteria:
    At least 18 years old, providing legally effective, written informed consent
    Willing and able to keep study appointments and follow instructions
    Good general health
    Willing to avoid sun and tanning lamp exposure during the study
Exclusion Criteria:
    History of abnormal response to UV radiation or sensitivity to any ingredient of the test products
    Sunburn, suntan, active dermal lesions, uneven skin tones or any condition such as nevi, blemishes or moles that might interfere with study procedures
    Use of any medication that might affect study results, e.g. photosensitizers, antihistamines, analgesics or anti-inflammatory drugs
    Pregnancy, nursing or any condition that might increase the risk of study participation
    Tanning bed or tanning lamp exposure in the last 3 months
Study Procedures:
    All procedures (product application, UV doses and evaluations) were performed with the subjects in the same position.
Day 1:
Subject Enrollment
    Prospective subjects reported to the testing laboratory and received a complete explanation of study procedures. If they desired to participate and agreed to the conditions of the study, subjects signed a written, witnessed consent form and a permission to release personal health information form, and provided a brief medical history. The back, between the beltline and shoulder blades, were examined for uneven skin tones and blemishes, using a Woods lamp. The technician completed the Subject History Form and qualified subjects were enrolled in the study. Subject numbers were assigned in the order of study enrollment.
MED Dose Administration
    A timed series of 5 UV doses, increasing in 25 percent increments, were administered to the mid-back, just below the shoulder blades and above the belt-line. UV doses for the MED, the time doses were completed and lamp readings were recorded on the MED form.

Subjects were instructed to avoid UV exposure, photosensitizers, analgesics, antihistamines and anti-inflammatory medications and to return to the testing laboratory 22 to 24 hours after completion of UV doses.

Day 2:

MED Determination

Subjects returned to the testing laboratory within 22 to 24 hours after completion of MED doses for evaluation of responses and were questioned non-directively to assess compliance, to identify concomitant medications and to monitor for adverse experiences. A trained evaluator graded responses of the UV exposed sites, under warm fluorescent or tungsten illumination of 450 to 550 lux, using the grading scale shown in Table 1.

TABLE 1

Grading Scale for Erythema Responses to UV Doses
Administered to Untreated Sites and Sunscreen Treated Sites

| | |
|---|---|
| 0 | No erythemal response |
| 1 | Minimally perceptible erythema |
| 2 | Mild erythema with clearly defined borders |
| 3 | Moderate erythema with sharp borders* |
| 4 | Dark red erythema with sharp borders* |
| 5 | Dark red erythema with sharp borders and possible edema* |
| 6 | Intense erythema with sharp borders and edema* |

*If moderate, dark red or intense erythema did not reach borders of exposed site, an explanation was to be provided in the comments section of evaluation forms The MED was determined as the first exposure site in the series that produces an erythema grade of at least 2 (Mild erythema with clearly defined borders). The progression of erythema grades was to be consistent with the UV doses administered.

If there were pronounced tanning responses, the subject was to be considered likely Type IV and not qualified for the study. In this case the subject was to be dropped from the study and replaced. Grades for each UV-exposed site, any comments and the evaluation time were recorded.

If required for practical scheduling, the subject was permitted to leave the testing laboratory at this point and return within one week for completion of Day 2 procedures.

Application of Products for SPF Determination

If the study participation of the subject has been interrupted, the subject was to be questioned non-directively to assess compliance, identify concomitant medications and monitor for adverse experiences.

The study technician drew 50 cm² rectangles in the designated locations on the subject's back between the belt-line and shoulder blades using a template and an indelible marker. The technician then applied 100 mg of test product in its designated rectangle and 100 mg of the HMS standard in an adjacent rectangle. The sunscreens were applied by "spotting" the material across the area and gently spreading, using a finger cot, until a uniform film is applied to the entire area.

The technician documented product formula designations, test site locations and application time.

UV Doses for Static SPF Determinations

After at least 15 minutes, the technician administered a series of 7 progressively increasing, timed UV doses to the sites treated with the test products. The dose series was determined by the product of the expected SPF of each test product, the subject's MED and the following number:

| Multiple of Subject's MED and Expected SPF (SPF > 15) | | | | | | |
|---|---|---|---|---|---|---|
| 0.76 | 0.87 | 0.93 | 1.00 | 1.07 | 1.15 | 1.32 |

The technician documented UV doses, times completed and lamp effective irradiance readings for each test product.

UV Doses for the HMS Standard

At least 15 minutes after the application of the HMS standard, the technician administered 7 progressively increasing timed UV doses to the HMS standard site. The dose series was determined by the product of the HMS standard SPF (4), the subject MED and the following numbers:

| Multiple of Subject MED and HMS Standard (SPF = 4) | | | | | | |
|---|---|---|---|---|---|---|
| 0.64 | 0.80 | 0.90 | 1.00 | 1.10 | 1.25 | 1.56 |

The technician documented the UV doses for the HMS standard, time completed and the lamp effective irradiance reading.

UV Doses for Repeat MED Determination

The technician administered a timed series of 5 UV doses, increasing by 25 percent increments, to an unprotected area of the mid-back. The series of 5 doses included the original MED in the center as follows:

| Multiple of Original MED | | | | |
|---|---|---|---|---|
| 0.64 | 0.80 | 1.00 | 1.25 | 1.56 |

UV doses for the repeat MED, time completed and the lamp effective irradiance were recorded.

The technician instructed subjects to return to the testing laboratory for evaluation within 22 to 24 hours after completion of the UV doses for the static SPF, HMS standard SPF and the repeat MED.

Day 3:

Evaluation of Responses to UV Doses for Static SPF and Repeat MED

Subjects returned to the testing laboratory and were questioned non-directively to assess compliance, to identify concomitant medications and to monitor for adverse experiences. A trained evaluator, who did not participate in product applications or administration of UV doses graded all sites that received UV doses, using the scale shown in Table 1. The technician who applied the test product and administered the UV doses was permitted to assist the evaluator, but the technician not permitted to influence the evaluator in the grading of UV responses. Grades of the responses of all sunscreen-treated sites were recorded.

SPF Computation:

The technician determined the repeat MED as above and computed the SPF values for each subject.

The final MED was to be the repeat MED, unless the repeat MED could not be determined. In that case the initial MED would be used as the final MED.

SPF values were calculated as the ratio of the MED for sunscreen-protected sites to the final MED.

The labeled SPF were calculated as follows, based on 20 subjects:

Mean SPF Value−A(rounded down to nearest whole number)

Where
$A = ts/\sqrt{n}$
$t$ = upper 5% of student's t distribution
$s$ = Standard Deviation
$n$ = Number of Subjects For the panel to be valid the SPF of the HMS standard sunscreen must fall within the standard deviation range of the expected SPF (i.e. 4.47±1.279) and the 95% confidence interval for the mean SPF of the HMS standard sunscreen must contain the value 4.

Adverse Experiences:

Any adverse experiences were to be documented in the subject file and immediate medical attention obtained if appropriate. Any serious adverse experience defined as life-threatening or requiring emergency measures was to be reported to the sponsor within 24 hours. All adverse experiences were to be reported to the sponsor.

Replacement of Subjects:

Any subject disqualified due to non-compliance or adverse experience was to be replaced. Subjects whose data did not permit successful computation of SPF values were to be replaced.

REFERENCES

1. U.S. Food and Drug Administration. Sunscreen Drug Products for Over-the-Counter Human Use; Final Monograph; 21CRF Parts 310, 352, 700 and 740. Federal Register 64 (98) May 21, 1999. pp. 27666-27693 d) a volatile coagent, the volatile coagent including at least one selected from the group consisting of dimethyl isosorbide, isopropyl myristate, pentylene glycol, and isopropyl myristate;

wherein:

the volatile coagent being capable of forming a complex with the active component to form a solubilized active component;

the complex being miscible in said siloxane matrix precursors;

the active component being mobile within a siloxane matrix such that the active component can move to the wound site;

the active component being a steroid compound in an amount ranging from 0.5 wt % to 3.0 wt % of the overall composition or an agent having sun screening activity, the agent having sun screening activity comprising octinoxate (ISP escalol 557) and octisalate (ISP escalol 587); and at least a portion of the volatile coagent evaporates from the preparation upon the formation of the siloxane matrix.

2. The spreadable preparation of claim 1, wherein the volatile coagent is an ester of a linear acid having a carbon chain length in the range of from about 6 to 13 carbon atoms and methanol, ethanol, or a secondary alcohol having a total carbon content in the range of from about 3 to about 8 carbon atoms.

LAMP CALIBRATIONS
Apr. 17, 2008
Calibration of Lamps 1, 2, 7, 8, 10 and 14 (Calibration Date)

| Range (nm) | Lamp 1 S/N 4533 Filter 010806 Bulb 322470 (Jan. 19, 2008) | Lamp 2 S/N 4534 Filter 05144 Bulb 322474 (Apr. 07, 2008) | Lamp 7 S/N 9533 Filter 080105 Bulb 323771 (Apr, 16, 2008) | Lamp 8 S/N 9560 Filter 121805 Bulb 323769 (Apr. 16, 2008) | Lamp 10 S/N 9655 Filter 081806C Bulb 323774 (Apr. 14, 2008) | Lamp 14 S/N 11476 Filter 07072-2 Bulb 323006 (Dec. 9, 2007) | Requirements Colipa 2006 [1] % | FDA 2007 [2] % |
|---|---|---|---|---|---|---|---|---|
| | | | Relative % contribution to erythemal effectiveness | | | | | |
| <290 | 0.01 | 0.00 | 0.087% | 0.012% | 0.019% | 0.01 | <0.1 | <0.1 |
| 290-300 | 5.8 | 4.7 | 6.7% | 6.5% | 4.7% | 7.1 | 1.0-8.O | 46.0-67.0 |
| 290-310 | 60.6 | 56.5 | 61.8% | 60.4% | 56.7% | 62.7 | 49.0-65.0 | |
| 29D-320 | 89.2 | 86.3 | 89.3% | 87.5% | 86.8% | 89.0 | 85.0-90.0 | 80.0-91.0 |
| 290-330 | 94.3 | 92.1 | 94.1% | 93.1% | 92.5% | 93.9 | 91.5-95.5 | 86.5-95.5 |
| 290-340 | 96.3 | 94.5 | 96.0% | 95.6% | 94.8% | 95.8 | 94.0-97-0 | 90.5-97.0 |
| 290-350 | 97.7 | 96.5 | 97.4% | 97.4% | 96.7% | 97.4 | — | 93.5-98.6 |
| 290-400 | 100.0 | 100.0 | 99.9% | 100.0% | 100.0% | 100.0 | 99.9-100 | 93.5-100.0 |
| | | | Ratios (%) | | | | | |
| UVAII/UV | 26.5 | 23.3 | 25.3 | 30.2% | 25.3 | 24.6 | ≥20 | — |
| UVAI/UV | 62.0 | 68.0 | 64.6 | 60.9% | 64.6 | 65.4 | ≥60 | — |
| | | | Absolute Values | | | | | |
| Total Power (mw/cm$^2$) | 98 | 111 | 96 | 128 | 138 | 147 | <150 | <150 |

I claim:

1. A spreadable preparation for aiding in wound healing and improving the characteristics of the post-epithelialially developed tissue at a wound site, the preparation comprising:
   a) a volatile component;
   b) siloxane matrix precursors capable of forming a siloxane matrix at temperatures in the range of from about 95 to 100 degrees Fahrenheit during evaporation of the volatile component and comprising an amount ranging from 25 wt % to 60 wt % of the overall spreadable preparation;
   c) an active component having low miscibility and low solubility in the siloxane matrix precursors; and 3. The spreadable preparation of claim 1, wherein the volatile coagent is a glycol comprised of a linear chain of three or more carbons and one or more hydroxyl group, and wherein said one or more hydroxyl group being on adjacent carbons, an end carbon, or an adjacent carbon and an end carbon.

4. The spreadable preparation of claim 1, wherein the active component comprises an agent having antihistamine or pain relieving activity.

5. The spreadable preparation of claim 1, wherein the agent having sun screening activity further comprises at least one or more selected from the group consisting of octocrylene (ISP escalol 597) and oxybenzone (ISP escalol 567).

6. The spreadable preparation of claim 1, wherein the steroid compound is hydrocortisone acetate USP.

7. The spreadable preparation of claim 1, wherein the siloxane matrix precursors comprise dimethicone crosspolymer, fumed silica, and dimethicone.

8. The spreadable preparation of claim 1, wherein the volatile component is a cyclic siloxane being present in the preparation at a concentration ranging from 12 wt % to 45 wt % of the overall preparation.

9. The spreadable preparation of claim 8, wherein the volatile component is cyclopentasiloxane.

10. A method for preparing the spreadable preparation of claim 1, the method comprising:
combining (i) the volatile component, (ii) the siloxane matrix precursors, (iii) the active component, and (iv) the volatile coagent to form a mixture;
wherein:
the siloxane matrix precursors are capable of forming a siloxane matrix at temperatures in the range of from about 95 to 100 degrees Fahrenheit during evaporation of the volatile component when the siloxane matrix precursors and the volatile component are combined;
the volatile coagent includes at least one selected from the group consisting of dimethyl isosorbide, isopropyl myristate, pentylene glycol, and isopropyl myristate, and the volatile coagent is capable of forming a complex with the active component to form a solubilized active component being miscible in said siloxane matrix precursors and mobile within the siloxane matrix such that said active component may move through the preparation to a wound site; and
at least a portion of said volatile coagent evaporates from the preparation upon the formation of the siloxane matrix.

11. A composition for topical application to a human subject in need thereof, the composition comprising:
a) a volatile component having a cyclic siloxane and being present in the composition at a concentration ranging from 12 wt % to 45 wt % of the overall composition;
b) siloxane matrix precursors having dimethicone and dimethicone cross polymers and ranging from 25 wt % to 60 wt % of the overall composition;
c) an active component comprising a steroid compound in an amount ranging from 0.5 wt % to 3.0 wt % of the overall composition; and
d) a glycol containing compound being present in the composition at a concentration ranging from 5 wt % to 50 wt % of the overall composition.

12. The composition of claim 11, wherein the steroid compound is hydrocortisone acetate USP in an amount ranging from 0.5 wt % to 1.0 wt % of the overall composition.

13. The spreadable preparation of claim 1, wherein the volatile component comprises a cyclic siloxane at a concentration ranging from 12 wt % to 45 wt % of the overall spreadable preparation.

* * * * *